(12) United States Patent
Olsen et al.

(10) Patent No.: US 8,292,899 B2
(45) Date of Patent: Oct. 23, 2012

(54) APPARATUS AND SYSTEM FOR ORTHOPEDIC FASTENER INSERTION AND EXTRACTION

(76) Inventors: Russell G. Olsen, Cedar City, UT (US); Steven S. Ramboz, Cedar City, UT (US)

( * ) Notice: Subject to any disclaimer, the term of this patent is extended or adjusted under 35 U.S.C. 154(b) by 519 days.

(21) Appl. No.: 12/467,175

(22) Filed: May 15, 2009

(65) Prior Publication Data
US 2009/0287225 A1  Nov. 19, 2009

Related U.S. Application Data

(60) Provisional application No. 61/053,581, filed on May 15, 2008.

(51) Int. Cl.
*B25B 23/10* (2006.01)
(52) U.S. Cl. ....................................... 606/104
(58) Field of Classification Search ............... 606/86 A, 606/86 B, 99, 104, 914, 916; 279/2.02, 2.17; 408/238–239 A; 600/562, 564, 567; 81/442, 81/444, 454
See application file for complete search history.

(56) References Cited

U.S. PATENT DOCUMENTS

| | | | |
|---|---|---|---|
| 954,073 A | 4/1910 | Bender |
| 1,039,751 A | 10/1912 | Ingram |
| 2,248,054 A | 7/1941 | Becker |
| 2,524,095 A | 11/1946 | Williams |
| 2,445,525 A | 7/1948 | Gulden |
| 2,496,309 A | 2/1950 | Pugh |
| 2,570,465 A | 10/1951 | Lundholm |
| 2,669,896 A | 2/1954 | Clough |
| 2,954,719 A | 10/1960 | Vaughn |
| 3,575,080 A | 4/1971 | Hannay |
| 3,604,487 A | 9/1971 | Gilbert |
| 3,641,866 A | 2/1972 | Mortensen |
| 4,140,111 A | 2/1979 | Morrill |
| 4,149,434 A | 4/1979 | Wilson |
| 4,228,723 A | 10/1980 | Cunningham |
| 4,581,962 A | 4/1986 | Marbourg |
| 4,776,328 A | 10/1988 | Frey et al. |
| 4,911,154 A | 3/1990 | Vickers |
| 5,020,519 A | 6/1991 | Hayes et al. |

(Continued)

FOREIGN PATENT DOCUMENTS
WO  9956662  11/1999
(Continued)

OTHER PUBLICATIONS

PCT/US2011/034968, International Search Report and Written Opinion, Jan. 6, 2012.

(Continued)

*Primary Examiner* — Brian E. Pellegrino
(74) *Attorney, Agent, or Firm* — Kunzler Law Group, PC

(57) ABSTRACT

An apparatus, system, and method are disclosed for positional fixation of a fastener, including but not limited to the extraction of an orthopedic screw. According to one embodiment, an instrument is provided which accepts a collet designed to conform to a proximal end of a variety of types and sizes of fasteners. The collet is installed through a chuck body, which is seated in a distal end of a handle. A closing mechanism within the handle causes the collet to tightly grip and lock onto the proximal end of the fastener. A compressible distal end of the collet may have longitudinal slits that define jaws for improving gripping flexibility.

20 Claims, 6 Drawing Sheets

U.S. PATENT DOCUMENTS

| | | | |
|---|---|---|---|
| 5,129,901 | A | 7/1992 | Decoste |
| 5,139,499 | A | 8/1992 | Small et al. |
| 5,214,987 | A | 6/1993 | Fenton, Sr. |
| 5,484,440 | A | 1/1996 | Allard |
| 5,531,750 | A | 7/1996 | Even-Esh |
| 5,649,931 | A | 7/1997 | Bryant et al. |
| 5,827,285 | A * | 10/1998 | Bramlet ............. 606/104 |
| 5,951,554 | A | 9/1999 | Holmes |
| 6,142,957 | A * | 11/2000 | Diamond et al. ........ 600/567 |
| 6,162,234 | A | 12/2000 | Freedland et al. |
| 6,302,632 | B1 | 10/2001 | Lin |
| 6,780,198 | B1 * | 8/2004 | Gregoire et al. ........ 606/104 |
| 6,827,722 | B1 * | 12/2004 | Schoenefeld ............ 606/104 |
| 6,860,889 | B2 | 3/2005 | Bonati et al. |
| 6,921,402 | B2 | 7/2005 | Contiliano et al. |
| 6,997,086 | B1 | 2/2006 | Graham |
| 7,073,415 | B2 * | 7/2006 | Casutt et al. .......... 606/104 |
| 7,090,680 | B2 | 8/2006 | Bonati et al. |
| 7,147,421 | B2 | 12/2006 | Suzuki |
| 7,204,838 | B2 | 4/2007 | Jackson |
| 7,452,361 | B2 | 11/2008 | Kreidler |
| 7,494,311 | B2 | 2/2009 | Fuerle |
| 7,938,044 | B2 * | 5/2011 | Ensign ............... 81/90.2 |
| 2003/0158555 | A1 | 8/2003 | Sanders et al. |
| 2004/0044345 | A1 | 3/2004 | DeMoss et al. |
| 2004/0220575 | A1 | 11/2004 | Biedermann et al. |
| 2005/0172762 | A1 | 8/2005 | Suzuki |
| 2005/0268757 | A1 | 12/2005 | Walker |
| 2005/0277923 | A1 | 12/2005 | Sweeney |
| 2006/0200147 | A1 | 9/2006 | Ensign et al. |
| 2007/0101835 | A1 | 5/2007 | Totsu |
| 2007/0123909 | A1 | 5/2007 | Rupp et al. |
| 2007/0213732 | A1 | 9/2007 | Khanna et al. |
| 2008/0249577 | A1 | 10/2008 | Dreyfuss |
| 2009/0054901 | A1 * | 2/2009 | Oh et al. ............. 606/99 |
| 2009/0176190 | A1 | 7/2009 | Ruiz-Vela et al. |
| 2009/0216282 | A1 | 8/2009 | Blake et al. |
| 2009/0257819 | A1 | 10/2009 | Burton |
| 2009/0260489 | A1 | 10/2009 | Siong |
| 2009/0270927 | A1 | 10/2009 | Perrow et al. |

FOREIGN PATENT DOCUMENTS

WO  2008-140289 A1  11/2008

OTHER PUBLICATIONS

U.S. Appl. No. 12/772,716 Office Action, Jan. 24, 2012.

U.S. Appl. No. 12/856,471 Office Action, Jan. 9, 2012.

* cited by examiner

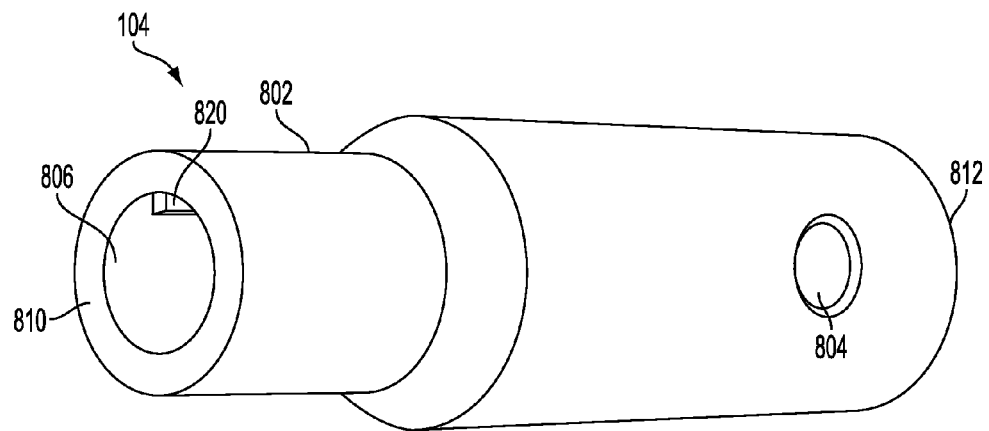
FIG. 8
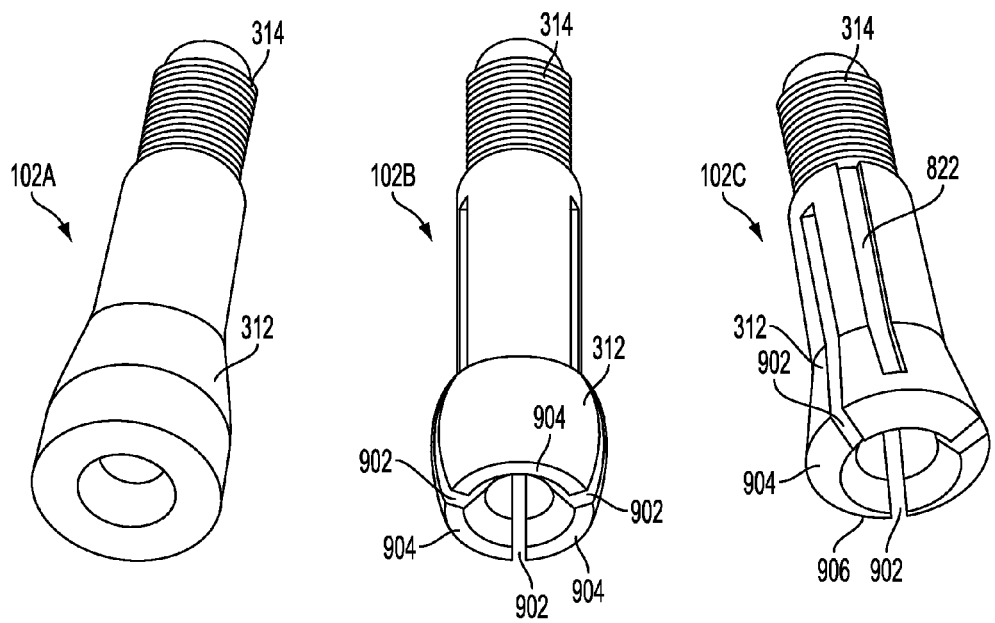
FIG. 9A
FIG. 9B
FIG. 9C

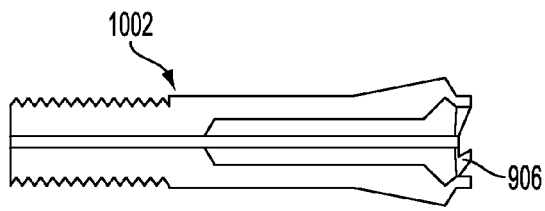
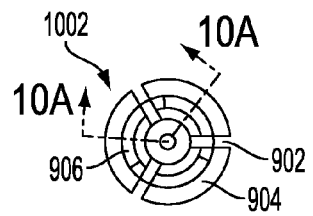
FIG. 10A  FIG. 10B
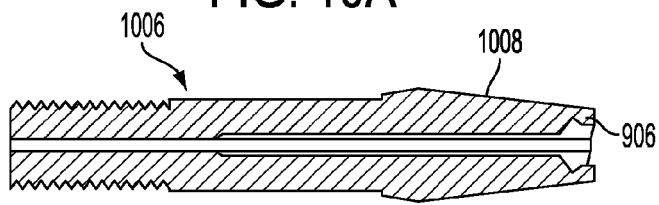
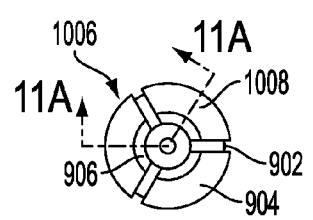
FIG. 11A  FIG. 11B
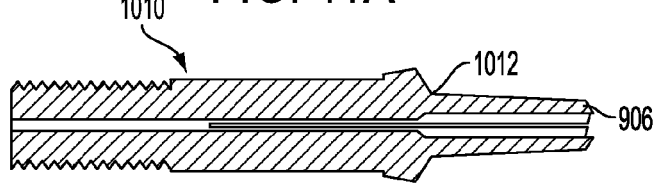
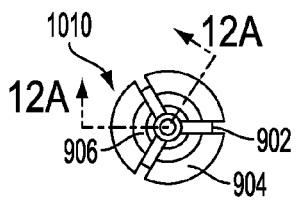
FIG. 12A  FIG. 12B
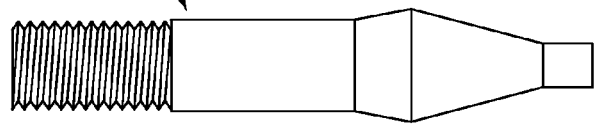
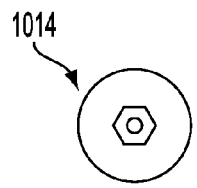
FIG. 13A  FIG. 13B
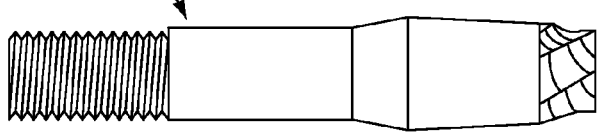
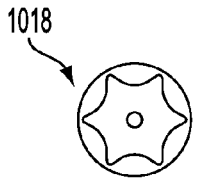
FIG. 14A  FIG. 14B
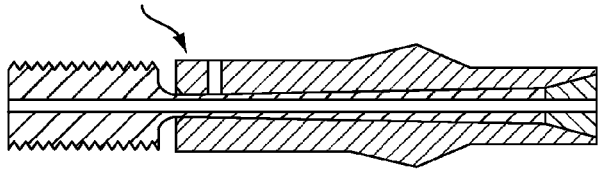
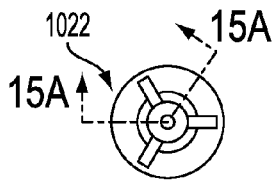
FIG. 15A  FIG. 15B

APPARATUS AND SYSTEM FOR ORTHOPEDIC FASTENER INSERTION AND EXTRACTION

CROSS-REFERENCE TO RELATED APPLICATION

This application claims the benefit of U.S. Provisional Patent Application No. 61/053,581, filed May 15, 2008, which is incorporated herein by reference.

FIELD

This invention relates to positional fixation and more particularly relates to orthopedic fixation devices.

BACKGROUND

The setting and immobilization of bone fractures with simple splints and slings has been practiced since ancient times. Modem biomedical engineering has yielded increasingly advanced orthopedic fixation technology, including various internal and external devices, such as pins, braces, plates, and screws. Many of these devices are temporary, and require removal after surgery or at any of various times throughout the healing process. Some devices such as internal screws are often left in place indefinitely, due to the cost, potential complications, and difficulty of removing them.

Typically, orthopedic hardware is removed at some time following surgery for various reasons. For example, a fastener embedded in bone can act as a stress riser, which may increase the risk of an undesired fracture in the bone proximate the fastener location. Additionally, over time, the position of a fastener can shift away from the initial embedded position, which may result in an infection or other negative side effect. At the very least, an un-removed fastener may simply cause discomfort, such as by conducting cold temperatures, or creating pain and irritation in the tissue surrounding the fastener. Although less likely, tan un-removed fastener may result in the potential inconvenience associated with metal detector false alarms.

In addition to potentially negative consequences caused by leaving hardware fixed in a patient's bone, some negative effects may be caused during the installation of the hardware. For example, a fastener may become damaged during the process of insertion, such as stripping the head or breaking the head off entirely. Such damage to the head can make further insertion and/or extraction of the fastener highly problematic.

The nature of bone itself also presents some challenges. As the bone heals, it tends to encase the fastener more tightly, which can increase the torque required to loosen the fastener from the bone. The bone may also encroach upon the head of the fastener making it difficult to access. Another problem arises from the hollow nature of bones. When removing a screw, once the threaded portion has been unscrewed from the distal cortex of the bone, there may be insufficient resistance offered by the screw head to keep the driver engaged. Moreover, even if the screw can be extracted to the point where the proximal end of the threaded portion comes into contact with the proximal cortex of the bone, the bone may have grown tightly around the shank, which can impede further progress. Accordingly, there may be insufficient resistance to keep the driver engaged in the head for the threads to bite.

Other challenges analogous to those discussed above may also exist in non-medical positional fixation applications, such as applications involving materials such as wood, metal, and plastic, or any applications where a reliable and minimally invasive apparatus, system, or method for insertion and/or removal of a fastener is desired.

SUMMARY

From the foregoing discussion, it should be apparent that a need exists for an apparatus, system, and method for the insertion and extraction of orthopedic fasteners which are problematically positioned or otherwise compromised. Beneficially, such an apparatus, system, and method would also be useful in non-medical applications.

The present invention has been developed in response to the present state of the art, and in particular, in response to the problems and needs in the art that have not yet been fully solved by currently available positional fixation instruments. Accordingly, the present invention has been developed to provide an apparatus, system, and method for positional fixation fastener operation, particularly extraction, which overcome at least one, many, or all of the above-discussed shortcomings in the art.

Generally, an apparatus is provided that tightens around a fastener, locks the fastener into position, and unlocks and releases the fastener when the operation is complete. The apparatus can include a collet with a proximal end and a distal end. In some embodiments, the distal end can be compressible or expandable to conform to a proximal end of a fastener. The proximal end of the collet is received by a chuck body. The apparatus can also include a handle configured to receive, such as in a seated arrangement, a proximal end of the chuck body. The apparatus may include a closing mechanism coupled to the handle. The closing mechanism can be operable to cause the collet to be tightened against the handle, which, in some embodiments, causes a compressible distal end of the collet to conform to the proximal end of the fastener.

In one embodiment, the closing mechanism may include a shaft longitudinally disposed within the handle for drawing the collet into the aperture of the chuck body so as to compress the collet around the proximal end of the fastener. A threaded connection between the shaft and a knob at a proximal end of the handle allows the collet to be tightened when the knob is turned in one direction, typically clockwise, and loosened when the knob is turned in an opposite direction.

In certain implementations, the closing mechanism includes a lever connected to a distal end of the handle at a first pivot joint, a locking member including a distal end connected to the lever at a second pivot joint proximal to the first pivot joint, and a shaft longitudinally disposed within the handle. The shaft can be coupled to the proximal end of the collet at a distal end portion of the shaft and coupled to a proximal end of the locking member at a third pivot joint proximal to the second pivot joint.

In a further implementation, the closing mechanism may also include a lever-operated linkage. The linkage may be comprised of a lever connected to a distal end of the handle by a first pivot joint, a locking member having a distal end connected to the lever by a second pivot joint proximal to the first pivot joint, and a proximal end connected through a channel in the side of the handle to the shaft by a third pivot joint. When the lever is depressed toward the handle, a proximal moment of force along the shaft draws the collet into the chuck body in a manner similar to the tightening of the above-described knob. Thus, the closing mechanism may comprise either the lever or the knob or both. When both are present, the knob permits an adjustment of the position of the third pivot joint to optimize the degree of force required to close the lever consistent with the strength of the operator and the structural integrity of the mechanism.

In the fully closed position, the lever causes the second pivot joint to descend deeper into the channel than a line between the first pivot joint and the third pivot joint, thus diverting a small amount of the compression force between the chuck body and the collet to create a downward moment of force locking the lever against the handle. To unlock the mechanism, the lever is lifted away from the handle, relaxing the proximal force along the shaft and loosening the collet by extending it out of the chuck body.

An ergonomic advantage may be obtained by allowing the lever to recess into the channel in the closed position, thereby permitting a more comfortable grip while using the instrument, as well as having the proximal end of the lever extend beyond the proximal end of the handle to facilitate lifting the lever out of the closed position.

According to one implementation, the collet and even the chuck body may be disposable. For example, biological contamination may prevent reuse of these components, even if treated, such as in an autoclave. Moreover, in some implementations, the apparatus may further include a centrally aligned longitudinal bore through all of the apparatus components to admit a wire for purposes of alignment with a cannulated fastener.

The apparatus, in one embodiment, is configured with a plurality of longitudinal slits in the compressible distal end of the collet, thereby forming a plurality of jaws. In some implementations, the jaws are able to flex outward to capture larger fasteners and flex inward under the compression force against the chuck body, thereby enabling a tighter grip on the proximal end of the fastener.

The apparatus is further configured, in one embodiment, with a cutting edge on the distal end of the collet. The cutting edge is able to remove material from around the proximal end of the fastener within a medium composed of the material, such as bone growth that has encroached upon it.

A system of the present invention is presented to operate compatibility with the wide variety of fasteners that exist or may be developed in the future. In particular, the system, in one embodiment, includes a plurality of interchangeable collets, each snugly conforming to the maximum perimeter of proximal end of a corresponding type or size of fastener. A special collet may even be provided to fit the shank of a broken fastener. In one specific implementation, a system for installing and removing fasteners from bone tissue includes a plurality of fasteners each comprising a proximal end portion having a different size. The system also includes a plurality of interchangeable collets each comprising a proximal end portion and a distal end portion. The distal end portion can be conformable to a perimeter of the proximal end portions of the plurality of fasteners. The system also includes a chuck body configured to receive the proximal end portion of each of the plurality of interchangeable collets and a handle configured to receive a proximal end of the chuck body. Additionally, the system includes a closing mechanism coupled to the handle. The closing mechanism includes a first tightening portion operable to partially conform the distal end portion of a respective collet to the perimeter of the proximal end portion of a respective fastener and a second tightening portion operable to further conform the distal end portion of the respective collet to the perimeter of the proximal end portion of the respective fastener.

In certain implementations, the first tightening portion comprises a rotatable knob and the second tightening portion comprises a pivotable lever. Rotation of the knob can cause the chuck body to apply a first force to the distal end portion of the respective collet and pivoting the lever can cause the chuck body to apply a second force to the distal end portion of the respective collet where the second force is greater than the first force A method of the present invention is also presented for positional fixation. In one embodiment, the method substantially includes the actions necessary to carry out the functions of the apparatus and system described herein. In one particular embodiment, a method for securing a fastener includes removably positioning a chuck body within a handle, removably positioning a proximal end of a collet within the chuck body, and removably positioning a fastener within a compressible distal end of the collet. The method also includes adjusting a tightening portion of a closing mechanism coupled to the handle and collet to urge the distal end of the collet against the chuck body and partially compress the distal end of the collet against the fastener. Further, the method includes adjusting a locking portion of the closing mechanism to further urge the distal end of the collet against the chuck body and further compress the distal end of the collet against the fastener.

In some implementations of the method, the tightening portion includes a knob coupled to the collet via a shaft. Adjusting the tightening portion can then include rotating the knob to urge the collet and shaft in a proximal direction. In other implementations, the locking portion includes a lever coupled to the collet via a shaft. Adjusting the locking portion can then include pivoting the lever toward the handle to urge the collet and shaft in a proximal direction.

In one embodiment, a method includes accessing a material amenable to positional fixation, installing the collet, fitting the fastener into the collet, tightening and locking the fastener into place, extracting the fastener by means of the handle, and then unlocking, loosening, and separating the fastener from the instrument. The method also may include inserting the fastener, particularly if the head is damaged, or if the torque required to fully insert a fastener, such as a screw, might strip the head if a conventional screwdriver were used. In a further embodiment, the method includes discarding the collet if it is not reusable, such as due to biological contamination.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the features, advantages, and characteristics of the apparatus, system, and method described herein may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only certain illustrative embodiments and are not therefore to be considered to be limiting of its scope, further embodiments of the invention will be described and explained with additional specificity and detail through the use of the specification, claims, and accompanying drawings, in which:

FIG. 8 is a detailed perspective view of a chuck body according to one embodiment;

FIGS. 9A-9C are a detailed perspective view of a plurality of collets according to several embodiments;

FIGS. 10A and 10B are a detailed cross-sectional side view taken along the line 10A-10A of FIG. 10B and a front view, respectively, of a collet according to a first embodiment;

FIGS. 11A and 11B are a detailed cross-sectional side view taken along the line 11A-11A of FIG. 11B and a front view, respectively, of a collet according to a second embodiment;

FIGS. 12A and 12B are a detailed cross-sectional side view taken along the line 12A-12A of FIG. 12B and a front view, respectively, of a collet according to a third embodiment;

FIGS. 13A and 13B are a side view and front view, respectively, of a collet according to a fourth embodiment;

FIGS. 14A and 14B are a side view and front view, respectively, of a collet according to a fifth embodiment;

FIGS. 15A and 15B are a detailed cross-sectional side view taken along the line 15A-15A of FIG. 15B and a front view, respectively, of a collet according to a sixth embodiment.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment. Furthermore, the described features, structures, or characteristics of the invention may be combined in any suitable manner in one or more embodiments. Additionally, one skilled in the relevant art will recognize that the invention may be practiced without one or more of the specific details described herein, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
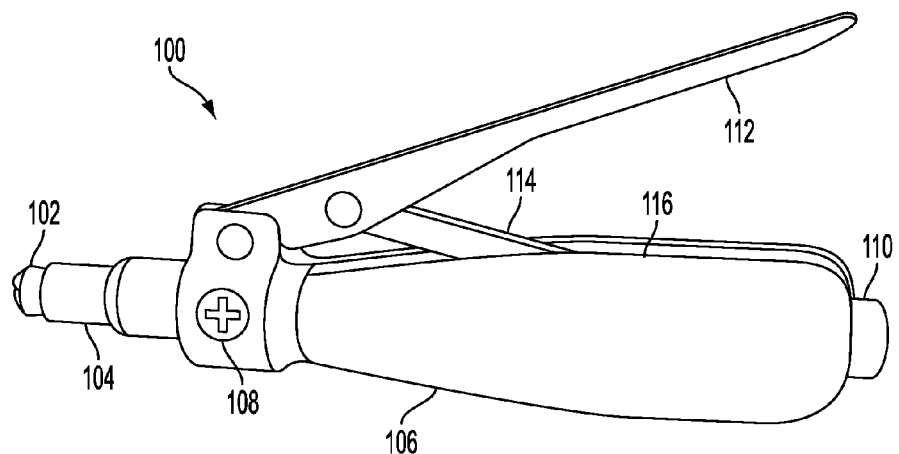
FIG. 1 is a perspective view illustrating one embodiment of a positional fixation instrument in accordance with the present invention.

Referring to FIG. 1, one embodiment of a positional fixation instrument 100 in accordance with the present invention is shown having an interchangeable collet 102 or chuck tip. The collet 102 is received by a chuck body 104 which is seated in a handle 106 and held in place by a set screw 108. The collet 102 may be tightened by adjusting a tightening portion and further tightened or locked in place by adjusting a locking portion. The tightening portion includes a knob 110 and is adjusted by turning the knob 110 in one direction, typically clockwise, to draw the collet 102 into the chuck body 104. The collet 102 may be opened and loosened by turning the knob 110 in an opposite direction, which extends the collet 102 out of the chuck body 104. The locking portion includes a lever 112 and locking member 114. The collet 102 maybe further tightened and locked by depressing lever 112, causing a locking member 114 to descend into a channel 116 along the side of the handle 106, and may be unlocked by lifting the lever 112.

Figure 2:
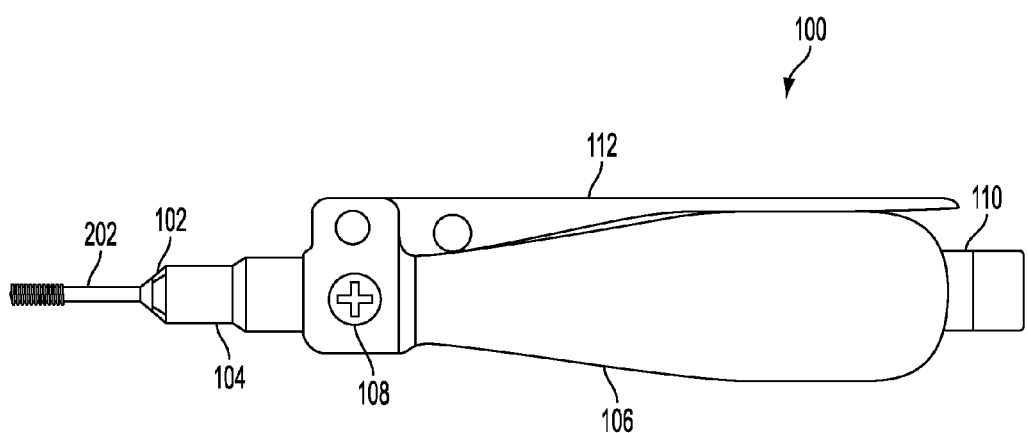
FIG. 2 is a side view further illustrating the instrument of FIG. 1 holding a fastener.

FIG. 2 is a side view further illustrating the instrument 100 holding a fastener 202. The lever 112 is in a fully closed and locked position, causing the collet 102 to close around and tightly grip the fastener 202. Note that in this configuration the lever 112 fits within the channel 116, thus providing an ergonomic handhold for operation of the instrument 100 in positioning the fastener 202.

Figure 3:
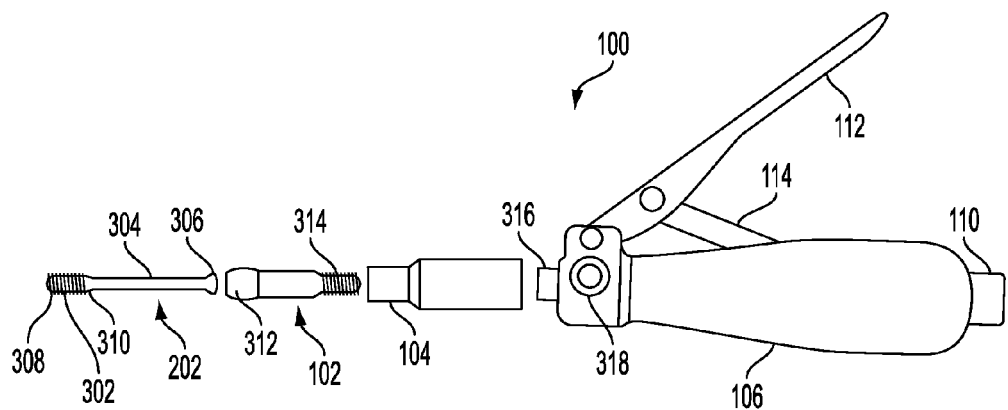
FIG. 3 is an exploded side view of the instrument and fastener of FIG. 2.

FIG. 3 is an exploded side view of the instrument 100 and the fastener 202. In one embodiment, the fastener 202 is a screw, having a threaded portion 302 connected via a shank 304 to a proximal end 306. Alternative embodiments of the fastener 202 may include a bolt, a pin, a rivet, a nail, a staple, an anchor, or some other fastener. The proximal end 306 as illustrated is a uniform sized head. Further embodiments of the proximal end 306 may include a non-uniform sized head or a headless fitting. In one embodiment, the threaded portion 302 may have a distal self-tapping or self-drilling end 308 to facilitate insertion of the fastener 202 by turning it in one direction, typically clockwise, and a proximal end 310 opposite the distal self-tapping end.

The collet 102 has a compressible distal end 312 which is designed to fit over and snugly conform in shape to the proximal end 306 of the fastener 202. In some embodiments, the collet 102 is configured to fit the proximal end 306 of a respectively sized and specific type of fastener. However, in other embodiments, the range of compression of the collet 102 allows the collet to fit several differently sized and/or types of fasteners. For example, in one specific implementation, the collet 102 is configured to fit over and snugly conform in shape to proximal ends 306 of fasteners 202 sized between about 6 mm and about 4.3 mm. Of course, in other implementations, the collet 102 can be sized to conform to proximal ends 306 of fasteners 202 within any of various size ranges. In some instances, larger proximal ends 306 may initially cause the compressible distal end 312 of the collet 102 to expand as the collet is placed about the proximal end to accommodate the larger size of the proximal end. However, tightening of the collet to the hand tool will cause the "expanded" compressible distal end to at least slightly compress to ensure a tight fit around the proximal end. A collet 1022 configured to expand as the collet is tightened to the hand tool is described below in relation to FIGS. 15A and 15B. In another embodiment, a specialized collet 102 may also be provided to fit a specifically sized shank 304 or differently sized shanks of the fastener 202 in the event that the proximal end 306 has broken off of the fastener.

The collet 102 is installed by inserting its threaded proximal end 314 through the chuck body 104 into a shaft 316 and screwing it firmly in place. The chuck body 104 is seated in the handle 106 and held in place by tightening the set screw 108 into a set screw hole 318 (set screw 108 not shown in FIG. 3). In the illustrated exploded view, part of the shaft 316 is visible through the set screw hole 318. As the shaft 316 is retracted into the handle by means of the knob 110 and/or the lever 112, the collet 102 is in turn drawn into the chuck body 104, thereby compressing the compressible distal end 312 and tightening its grip around the corresponding proximal end 306 of the fastener 202.

Figure 4:
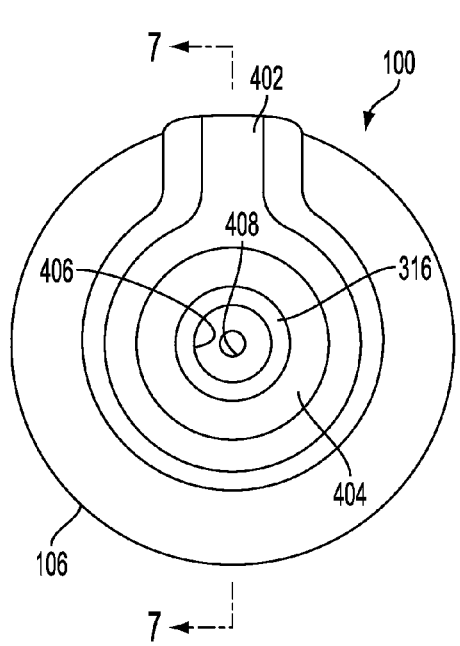
FIG. 4 is a front view of the instrument of FIG. 1.

FIG. 4 is a front view of the instrument 100, with the chuck body removed to better reveal its internal structure. As shown with the lever 112 in the closed position, the handle 106 is roughly cylindrical in shape, with the lever mount 402 on top. In alternative embodiments, the handle can have any of various shapes, such as ovular, triangular, elliptical, and hexagonal. The chuck seat 404 is countersunk into the handle 106 to receive the chuck body 104 as it encircles the shaft 316. A threaded hole 406 is provided in the shaft 316 to accept the threaded proximal end 314 of the collet 102. A central bore 408 runs the length of the instrument 100 to allow passage of a guide wire (not shown) as used in conjunction with a cannulated fastener. Accordingly, the collet 102, chuck body 104, handle 106, shaft 316, and knob 110 include central bores that collectively define the bore 408.

Figure 5:
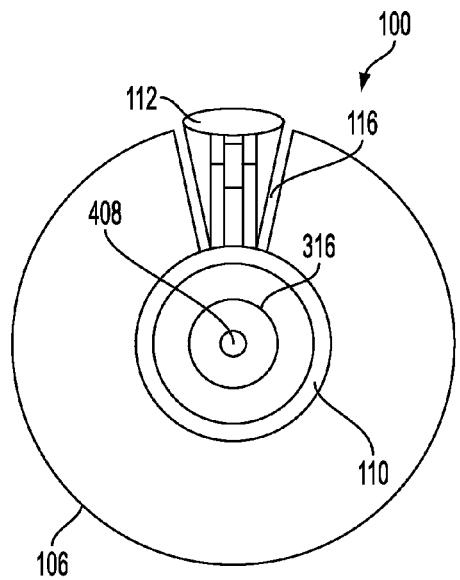
FIG. 5 is a rear view of the instrument of FIG. 1.

FIG. 5 is a rear view of the instrument 100, providing a clear illustration of the channel 116 in line with the lever 112. It can be seen that the knob 110 is hollow, being connected to the shaft 316, thereby retracting or extending the collet 102 via the threaded hole 406 in the shaft 316 when the knob 110 is respectively turned in one direction or another. The central bore 408 is also visible in this view, since it passes all the way through the shaft 316 and emerges into the hollow knob 110.

Figure 6:
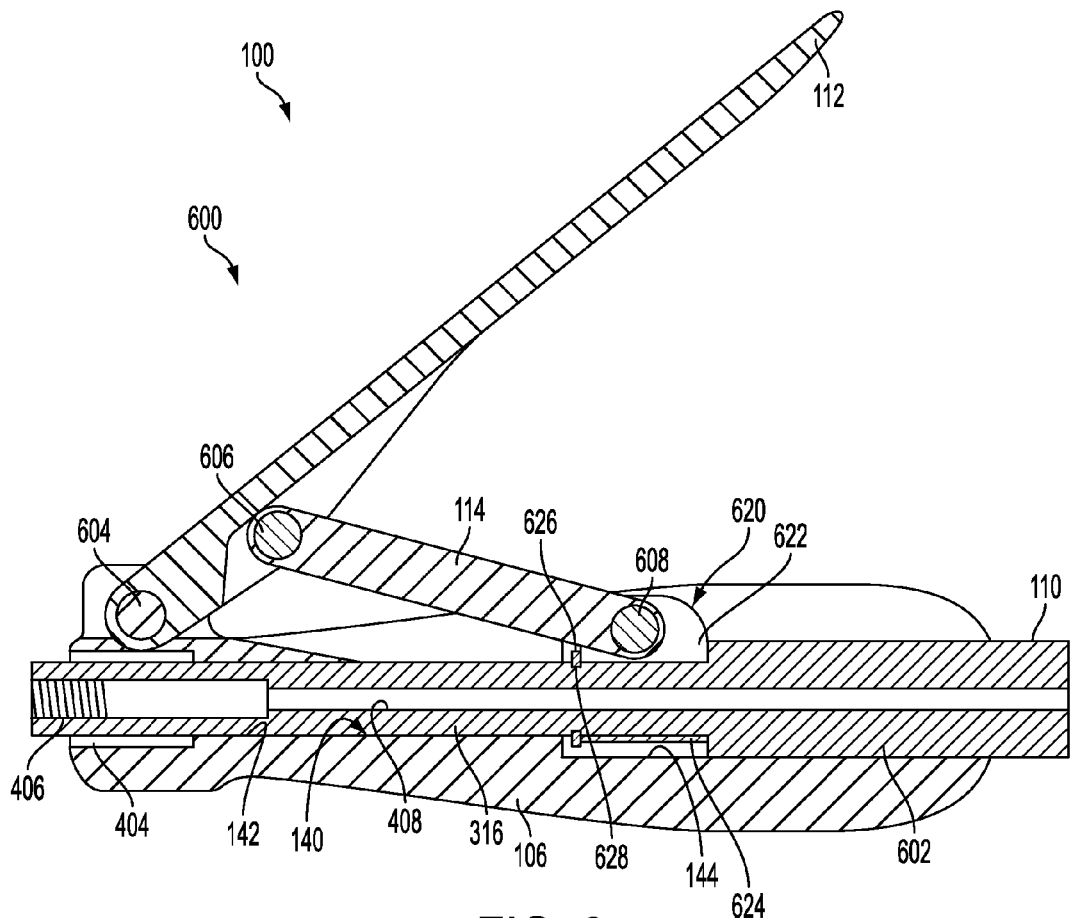
FIG. 6 is a cross-sectional side view of the instrument of FIG. 1 taken along the line 6-6 of FIG. 4 and showing a closing mechanism in an open position.

As shown in FIG. 6, the knob 110 of instrument 100 is coupled to the shaft 316 via an extended portion 602. In the illustrated embodiment, the knob 110, shaft 316, and extended portion 602 form a one-piece monolithic construction with each other. The handle 106 includes a central bore 140 having a first proximal portion 142 coaxial with a second distal portion 144. The first proximal portion 142 is sized to matingly receive the shaft 316 and the second distal portion 144 is sized to matingly receive the extended portion 602 of the knob 110. The shaft 316 and extended portion 602 are rotatable within the first proximal and second distal portions 142, 144, respectively. Preferably, the first proximal portion 142 retains the shaft is substantially coaxial alignment with the first proximal portion and the second distal portion 144 retains the extended portion is substantially coaxial alignment with the second distal portion. The lever 112 is connected to the handle 106 via a first pivot joint 604. A second pivot joint 606 connects the lever 112 to a distal end of the locking member 114. A proximal end of the locking member 114 is in turn connected to the extended portion 602 of the knob 110 via a third pivot joint 608. The chuck seat 404 and central bore 408 are also shown in this view.

The proximal end of the locking member 114 is secured to the third pivot joint 608 via a shackle member 620 coupled to the shaft 316. The shackle member 620 is configured to ensure that the third pivot joint 608 moves axially when the shaft 316 moves axially, and that the shaft 316 is rotatable relative to the third pivot joint. The shackle member 620 includes two space-apart tabs 622 extending vertically away from the shaft 316 and a sleeve portion 624 wrapped about at least half of the periphery of the shaft. The proximal end of the locking member 114 is positioned between the tabs 622 and secured to the tabs by extending the pivot joint 608 through apertures in the tabs and locking member. When secured to the proximal end of the locking member 114, the shackle member 620 is configured to retain the third pivot joint 608 in a vertically fixed location (as shown in FIG. 6) relative to the shaft 316, but allow the shaft to rotate relative to the shackle member. The shackle member 620 is prevented from moving axially or horizontally (as shown in FIG. 6) relative to the shaft 316 through use of a stop 626 secured to and fixed relative to the shaft and extended portion 602. More specifically, the shackle member 620 is effectively sandwiched between the stop 626 and the extended portion 602 of the knob 110. The stop 626 prevents movement of the shackle member 620 in a first axial direction relative to the shaft 316 and the extended portion 602 prevents movement in a second axial direction opposite the first relative to the shaft. The stop 626 transfers collet disengaging thrust loading from the lever 114 to the shaft 316 when releasing a fastener from the collet and the extended portion 602 transfers collet engaging thrust loading from the lever 114 to the shaft 316 when securing a fastener in the collet. In one specific embodiment, the stop 626 is an external snap ring engaged within a recess 628 formed in the outer surface of the shaft 316.

Figure 7:
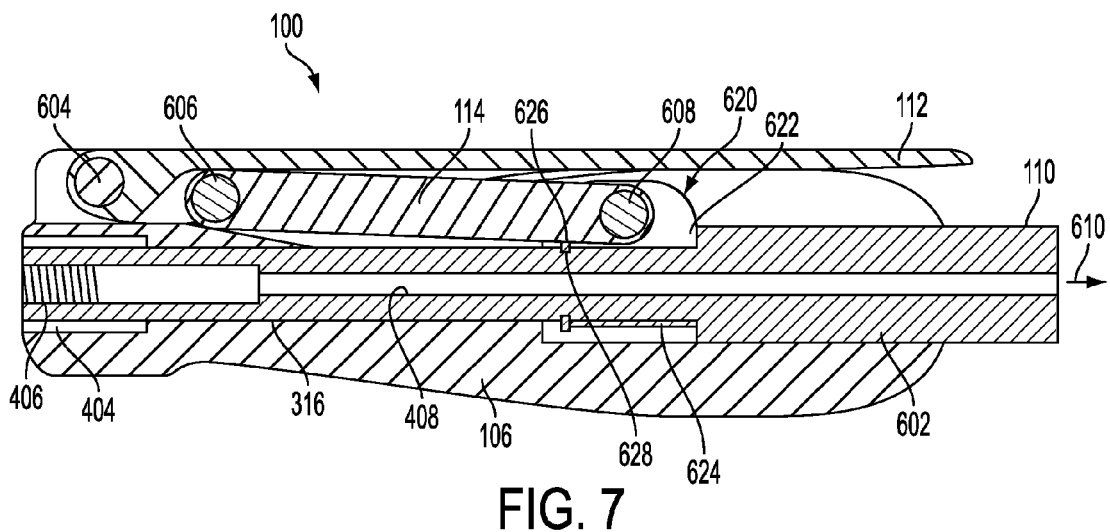
FIG. 7 is a cross-sectional side view of the closing mechanism of FIG. 6 in a closed position.

Referring to FIG. 7, as the lever 112 is depressed, the second pivot joint 606 is brought directly into line with the first pivot joint 604 and the third pivot joint 608 to drive the shaft 316 and knob 110 in a proximal direction, i.e., distal-to-proximal direction, as indicated by directional arrow 610. Movement of the shaft 316 and knob 110 in the proximal direction after the collet has been tightened against the chuck body 104 using the knob results in the application of a maximal compression force between the compressible distal end 312 of the collet 102 and the chuck body 104 as described above. When the lever 112 is in the fully closed position as shown, the second pivot joint 606 is substantially aligned with, but slightly below a line between, the first pivot joint 604 and third pivot joint 608, thus diverting a small amount of the maximal compression force into a downward moment of force which holds the lever 112 down and locks the closing mechanism 600 in the fully closed position. Note that the lever 112 extends proximally beyond the handle 106, providing convenient access for lifting it to unlock the closing mechanism 600.

As shown in FIG. 8, a central bore 806 runs a length of the chuck body 104 from a distal end 810 to a proximal end 812. The chuck body 104 includes a collet engaging portion 802 extending from the distal end 810 to a location intermediate the distal end and proximal end 812. The central bore 806 along the collet engaging portion 802 is inwardly tapered in a distal end to proximal end direction. The taper of the central bore 806 approximately corresponds with a distal-to-proximal taper of the outer surface of the compressible distal end of a collet in an uncompressed state (see, e.g., distal end 312 of collet 102C of FIG. 9C). When initially assembled, the corresponding tapered surfaces of the central bore 806 and distal end 312 of the collet engage each other such that the distal end 812 of the collet 102C matingly seats within the central bore. As the lever 112 is closed, the compressible distal end 312 of the collet slides along the central bore 806 of the collet engaging portion 802 in the distal-to-proximal direction relative to the central bore such that the wall of the central bore exerts an inwardly directed force against the compressible distal end of the collet. The inwardly directed force causes the compressible distal end 312 of the collet 102C to gradually deform and radially compress against the proximal end 306 of the fastener 202. The tapered nature of the engaging surfaces distributes the inwardly directed force evenly across the distal end 312 of the collet 102C to facilitate ease in compressing the distal end against the fastener. The tapered surface of the central bore 806 is also configured to engage and facilitate compression of a distal end of a collet having a curved or arcuate shaped outer surface (see, e.g., distal end 312 of collet 102 of FIG. 3 and distal end 312 of collet 102B of FIG. 9B).

The chuck body 104 also includes a key or spline 820 extending inwardly from the inner surface of the central bore 806 in a direction parallel to the axis of the chuck body. The key 820 can extend between the distal end 810 to a location intermediate the distal end 810 and the proximal end 812. The key 820 is configured to engage a keyway or slot 822 formed in the collet and extending in a direction parallel to the axis of the collet (see, e.g., collet 102C of FIG. 9C). In other words, as the collet is inserted into the chuck body 104, the key 820 is positioned and retained within the keyway 822. Engagement between the key 820 and keyway 822 reduces, restricts, or prevents rotation of the collet relative to the chuck body 104. Additionally, the key 820 and keyway 822 are axially aligned when the collet is properly seated in the chuck body. The axial alignment between the key and keyway allows for relative movement between the collet and chuck body in the axial or lengthwise direction. Although in the illustrated embodiments, the key 820 is formed in the central bore 806 of the chuck body 104 and the keyway is formed in the collet 102C, in other embodiments, the key can be formed in the collet and the keyway can be formed in the central bore.

In alternative embodiments, configurations other than a key-keyway or spline configuration can be used to reduce, restrict, or prevent relative rotation between the chuck body and collet. For example, in certain implementations, a portion of the central bore 806 can have an out-of-round cross-sectional shape and the outer surface of the collet can have an out-of-round shape at least approximately matching the out-of-round cross-sectional shape of the central bore. When the collet is inserted into the central bore 806, the out-of-round portion of the collet can be positioned within and matingly engage the out-of-round portion of the central bore 806. Because the portions of the central bore 806 and collet are out-of-round, engagement between them at least restricts rotation of the collet relative to the chuck body 104. In specific implementations, the out-of-round shape can be any of various shapes, such as hexagonal, triangular, rectangular, and ovular.

Also shown is FIG. 8 is a set screw depression 804 formed in an outer surface of the chuck body 104. The depression 804 is configured to engage the set screw 108 thereby holding the chuck body 104 firmly in place within the chuck seat 404 (see FIG. 6).

FIGS. 9A-9C are detailed perspective views of a plurality of collets 102A-102C. Collets 102B, 102C include longitudinal slits 902 cut in the compressible distal end 312 thereby forming jaws 904. The jaws 904 are able to flex inward under the compression force from the chuck body 104, thereby enabling a tight grip on the proximal end 306 of the fastener 202. The slits 902 are narrow enough not to compromise the snug conformity or tight fit between the collets 102B, 102C and the proximal end 306 of the fastener 202.

As shown in FIG. 9C, the jaw 904 of collet 102C may have a cutting edge 906 configured to remove material from around the proximal end 306 of the fastener 202. For example, the material may be bone which has grown around the edges of the proximal end 306 and must be cut away in order to expose enough of the fastener 202 to achieve a tight grip necessary for extracting the fastener. The collet 102C can be rotated while applying a force to the collet directed toward the material to be removed. As the collet 102C is rotated, the cutting edge 906 cuts through the material.

FIGS. 10A and 10B show a detailed side cutaway view and front view, respectively, of a collet 1002. The collet 1002 is a radial engagement (RE) type collet with longitudinal slits 902 and short clearance cutters each having a cutting edge 906. FIGS. 11A and 11B show a detailed side cutaway view and front view, respectively, of a collet 1006. The collet 1006 is an RE type collet with a clearance cutting body 1008, a cutting edge 906, and longitudinal slits 902. FIGS. 12A and 12B show a detailed side cutaway view and front view, respectively, of a collet 1010. The collet 1010 is an RE type collet with a tor engage screw shank boring body 1012, a cutting edge 906, and longitudinal slits 902. FIGS. 13A and 13B show a side view and front view, respectively, of a collet 1014. The collet 1014 is a hex drive solid collet without a compressible distal end. FIGS. 14A and 14B show a side view and front view, respectively, of a collet 1018. The collet 1018 is an "easy-out" type extractor solid collet without a compressible distal end. The distal ends of the collets 1014, 1018 are not compressible, but include recesses for receiving a standard sized fastener head.

Solid collets, such as collets 1014, 1018 are usable to insert a fastener having a standard head into bone tissue and to extract the fastener if the head has not broken away from the shank. As discussed above, if the head has indeed broken away from the shank or extracting the fastener by gripping the shank is more desirable, a collet having a compressible distal end may be more desirable.

FIGS. 15A and 15B show a detailed side cutaway view and front view, respectively, of a collet 1022. The collet 1022 is an expandable tip collet for gripping hollow fasteners and non-fasteners from the inside of the fasteners and non-fasteners, respectively. For example, the tip of the collet 1022 can be inserted into the hollow interior of an embedded fastener. As the threaded proximal end of the collet 1022 is rotated and moved proximally via the hand tool 100 as discussed above, an interior member secured to the threaded proximal end correspondingly rotates and moves relative to an exterior member, which is prevented from proximal movement via the chuck body 104. The distal tip of the interior member is beveled such that as it moves proximally relative to the exterior member, it causes the exterior member to expand outwardly until it tightly grips an interior surface of the hollow fastener. The embedded fastener can then be removed by pulling or rotating the hand tool 100.

Like the hand tool 100, the collets described herein can each have a central bore running the length of the collets to allow for passage of a guide wire as used in conjunction with a cannulated fastener (see, e.g., collets 1002-1022 of FIGS. 10A-15B). In this manner, a guide wire can extend through the bore 408 in the hand tool 100, the collet, and the fastener.

The components of the instruments 100 can be made from any of various materials. For example, in some embodiments, each of the components is made from a metal or metal alloy, such as steel, stainless steel, and/or aluminum. Also, one or more components can be made from a high-strength plastic or polymer.

Figure 16:
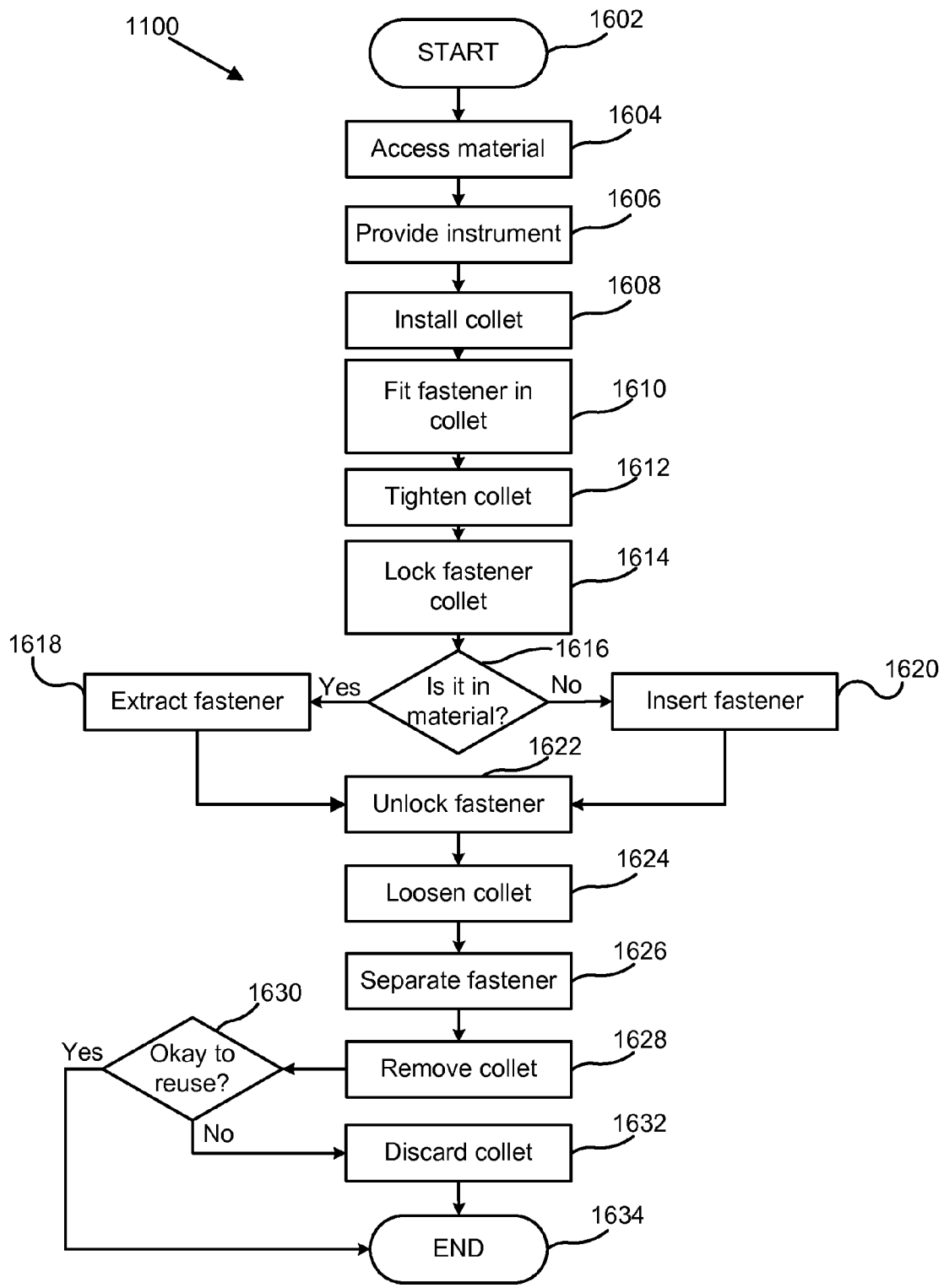
FIG. 16 is a flow diagram illustrating one embodiment of a method for employing the instrument in accordance with the present invention.

FIG. 16 is a flow diagram illustrating one embodiment of a method 1600 for employing a fastener extraction and insertion instrument, such as instrument 100, in accordance with the present invention. The method 1600 starts 1602 by accessing 1604 material requiring positional fixation or in which a fastener is positionally fixed. The method 1600 proceeds by providing 1606 an instrument (e.g., instrument 100) and installing 1608 a collet (e.g., collet 102) in the instrument. A proximal end of a fastener (e.g., proximal end 306 of fastener 202) is then fitted 1610 into a snugly conforming compressible distal end (e.g., end 312) of the collet. The proximal end of the fastener is partially tightened 1612 within the collet by adjusting a tightening portion of a closing mechanism, e.g., turning a knob (e.g., knob 110) in a tightening direction. Adjusting the tightening portion urges the distal end of the collet against a chuck body of the instrument and partially compresses the distal end of the collet against the fastener. The proximal end of the fastener is fully tightened and locked 1614 in place by adjusting a locking portion, e.g., depressing a lever (e.g., lever 112). Adjusting the locking portion further urges the distal end of the collet against the chuck body and further compresses the distal end of the collet against the fastener.

If the fastener is already embedded in the material, then it is extracted 1618 by operating a handle (e.g., 106) of the instrument, such as pulling the handle away from the material. If the fastener 202 is not embedded or only partially embedded in the material, then the fastener is inserted 1620 inserted into the material to completely embed the fastener in the material by operating the handle, such as pushing the handle toward the material. When the extraction 1618 or insertion 1620 of the fastener is complete, then the fastener is at least partially loosened or unlocked 1622 from the instrument by lifting the lever and, if necessary, further loosened by loosening 1624 the collet by turning the knob in a loosening direction opposite the tightening direction. Unlocking 1622 the fastener and further loosening 1624 the collet allows the fastener to be separated 1626 from the collet. The collet is then removed 1628 from the instrument. If the collet can be reused as determined at 1630, then the method ends 1634. However, if the collet cannot be reused, such as due to contamination, as determined at 1630, then the collet may be discarded 1632 prior to the end 1634 of the method 1600.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A hand tool comprising:
a collet having a proximal end and a distal end, the distal end being engageable with a proximal end of a fastener;
a chuck body configured to receive the proximal end of the collet;
a handle configured to receive a proximal end the chuck body; and
a closing mechanism coupled to the handle, the closing mechanism being operable to forcibly secure the proximal end of the collet against the chuck body to engage the distal end of the collet with the proximal end of the fastener;
wherein the closing mechanism comprises a knob and a shaft disposed within the handle, the shaft being threadably coupled to the proximal end of the collet at a first end and co-rotatably coupled to the knob at a second end, and wherein rotation of the knob in a first direction rotates the shaft in the first direction and moves the collet in a proximal direction against the chuck body via the threaded coupling between the first end of the shaft and proximal end of the collet, and rotation of the knob in a second direction opposite the first direction rotates the shaft in the second direction and moves the collet in a distal direction away from the chuck body via the threaded coupling between the first end of the shaft and the proximal end of the collet; and
wherein the closing mechanism further comprises a lever pivotally coupled to the handle and coupled to the shaft via a locking member, and wherein the lever is pivotable in a third direction relative to the handle to move the shaft in the distal direction along the handle and move the collet in the distal direction against the chuck body, and pivotable in a fourth direction relative to the handle, the fourth direction being opposite the third direction, to move the shaft in the proximal direction along the handle and move the collet in the proximal direction away from the chuck body.

2. The hand tool of claim 1, wherein the distal end comprises a deformable distal end, and wherein the closing mechanisms is operable to cause the deformable distal end of the collet to conform to the proximal end of the fastener.

3. The hand tool of claim 2, wherein the deformable distal end comprises a compressible distal end.

4. The hand tool of claim 2, wherein the deformable distal end comprises an expandable distal end.

5. The hand tool of claim 2, wherein the deformable distal end of the collet is deformable to conform to the proximal ends of a plurality of fasteners, and wherein each of the proximal ends of the plurality of fasteners is differently sized.

6. The tool of claim 1, wherein the distal end of the collet is configured to be engageable with a proximal end of the fastener selected from the group consisting of a uniform sized head, a non-uniform sized head, a headless fitting, and a shank.

7. The tool of claim 1, wherein the compressible distal end of the collet comprises a plurality of longitudinal slits and a plurality of jaws defined between the slits.

8. The tool of claim 1, wherein the fastener is embeddable within a medium, and wherein the compressible distal end of the collet comprises a cutting edge configured to remove a portion of the medium from around the proximal end of the fastener when the fastener is embedded within the medium.

9. The tool of claim 8, wherein the medium comprises bone tissue, the compressible distal end of the collet comprising a cutting edge configured to remove a portion of the bone tissue from around the proximal end of the fastener when the fastener is embedded within the bone tissue.

10. The tool of claim 1, wherein:
the lever is connected to a distal end of the handle at a first pivot joint;

the locking member comprises a distal end connected to the lever at a second pivot joint proximal to the first pivot joint; and the shaft is longitudinally disposed within the handle, the shaft being coupled to the proximal end of the collet at a distal end portion of the shaft and coupled to a proximal end of the locking member at a third pivot joint proximal to the second pivot joint.

11. The tool of claim 10, wherein the first, second, and third pivot joints are not aligned with each other in an open position, and the first, second, and third pivot joints are substantially aligned in the closed position.

12. The tool of claim 11, wherein the handle comprises a longitudinal channel formed in a side of the handle, and wherein the lever is at least partially positionable within the longitudinal channel in a closed position.

13. The tool of claim 11, wherein a proximal end of the lever extends proximally beyond a proximal end of the handle in a closed position.

14. The tool of claim 11, wherein an outer surface of the lever is approximately flush with an outer surface of the handle in a closed position.

15. The tool of claim 1, wherein the distal end of the collet is configured to be engageable with a fastener having a distal end comprising a self-threading threaded portion.

16. The tool of claim 1, further comprising a centrally aligned longitudinal bore extending through the collet, chuck body, handle, and closing mechanism, the bore being configured to receive a cannulated fastener wire.

17. The tool of claim 1, wherein the collet is removable from the chuck body and the chuck body is removable from the handle.

18. A system for installing and removing fasteners from bone tissue, the system comprising:

a plurality of interchangeable collets each comprising a proximal end portion having threads and a distal end portion, the distal end portion of each of the plurality of interchangeable collets being conformable to a proximal end portion of at least one of a plurality of fasteners;

a chuck body configured to receive the proximal end portion of each of the plurality of interchangeable collets;

a handle configured to receive a proximal end portion of the chuck body; and a closing mechanism coupled to the handle, the closing mechanism comprising:

a shaft disposed within the handle, the shaft comprising a threaded aperture that is threadably coupleable with the threads of the proximal end portion of the plurality of interchangeable collets;

a rotatable knob co-rotatably coupled to the shaft, the rotatable knob being rotatable relative to the handle to partially conform the distal end portion of a respective collet to the proximal end portion of a respective fastener; and a pivotable lever that is pivotable to further conform the distal end portion of the respective collet to the proximal end portion of the respective fastener.

19. The system of claim 18, wherein rotation of the knob causes the chuck body to apply a first force to the distal end portion of the respective collet and pivoting the lever causes the chuck body to apply a second force to the distal end portion of the respective collet, the second force being greater than the first force.

20. A hand tool comprising:

a collet having a proximal end portion with threads and a distal end portion, the distal end portion being engageable with a proximal end portion of a fastener;

a chuck body configured to receive the proximal end portion of the collet;

a handle configured to receive a proximal end portion the chuck body; and a closing mechanism coupled to the handle, the closing mechanism being operable to forcibly secure the proximal end portion of the collet against the chuck body to engage the distal end portion of the collet with the proximal end portion of the fastener, wherein the closing mechanism comprises:

a shaft disposed within the handle, the shaft comprising a threaded aperture that is threadably coupleable with the threads of the proximal end portion of the collet;

a rotatable knob co-rotatably coupled to the shaft, the rotatable knob being rotatable relative to the handle to partially conform the distal end portion of the collet to the proximal end portion of the fastener; and a pivotable lever that is pivotable to further conform the distal end portion of the collet to the proximal end portion of the fastener.

* * * * *

UNITED STATES PATENT AND TRADEMARK OFFICE
CERTIFICATE OF CORRECTION

PATENT NO.        : 8,292,899 B2                                    Page 1 of 1
APPLICATION NO.   : 12/467175
DATED             : October 23, 2012
INVENTOR(S)       : Russell G. Olsen It is certified that error appears in the above-identified patent and that said Letters Patent is hereby corrected as shown below:

Column 1, Line 39
  "Although less likely, tan un-removed"---should read "Although less likely, an un-removed"

Column 12, Line 3
  "end the chuck"---should read "end of the chuck"

Column 12, Line 37
  "mechanisms is operable"---should read "mechanism is operable"

Signed and Sealed this
Fourth Day of December, 2012

David J. Kappos
*Director of the United States Patent and Trademark Office*